United States Patent [19]

Bon

[11] 4,090,924

[45] May 23, 1978

[54] METHOD TO DETERMINE THE SUITABILITY OF DIAPHRAGM FOR USE IN AN ELECTROLYTIC CELL

[75] Inventor: Charles K. Bon, Midland, Mich.

[73] Assignee: The Dow Chemical Company, Midland, Mich.

[21] Appl. No.: 733,630

[22] Filed: Oct. 18, 1976

Related U.S. Application Data

[63] Continuation-in-part of Ser. No. 517,570, Oct. 24, 1974, abandoned.

[51] Int. Cl.² .......................................... G01N 27/46
[52] U.S. Cl. ............................. 204/1 T; 204/195 R; 204/295; 204/98; 204/64 T
[58] Field of Search ................... 204/1 T, 195 R, 295

[56] References Cited

U.S. PATENT DOCUMENTS

| | | | |
|---|---|---|---|
| 1,700,796 | 2/1929 | Hake | 204/195 F |
| 3,011,964 | 12/1961 | Guillot | 204/295 |
| 3,098,802 | 7/1963 | Beer | 204/295 |

OTHER PUBLICATIONS

"Test Manual (Tentative) for Permselective Membranes." Distributed by National Technical Information Service, Jan. 1964, pp. 156–163, 189–200.

Primary Examiner—T. Tung
Attorney, Agent, or Firm—J. M. Kuszaj; R. W. Selby

[57] ABSTRACT

An electrical method to determine the suitability of a diaphragm for use in an electrolytic cell. The method comprises inserting the diaphragm between a primary anode and a primary cathode immersed in an electrolyte and then impressing a known direct current electromotive force between the electrodes. The change in electrical properties across the electrolyte resulting from insertion of the diaphragm is determined. Such change is indicative of the suitability of the diaphragm for use in an electrolytic cell and can be a measure of diaphragm uniformity.

16 Claims, 1 Drawing Figure

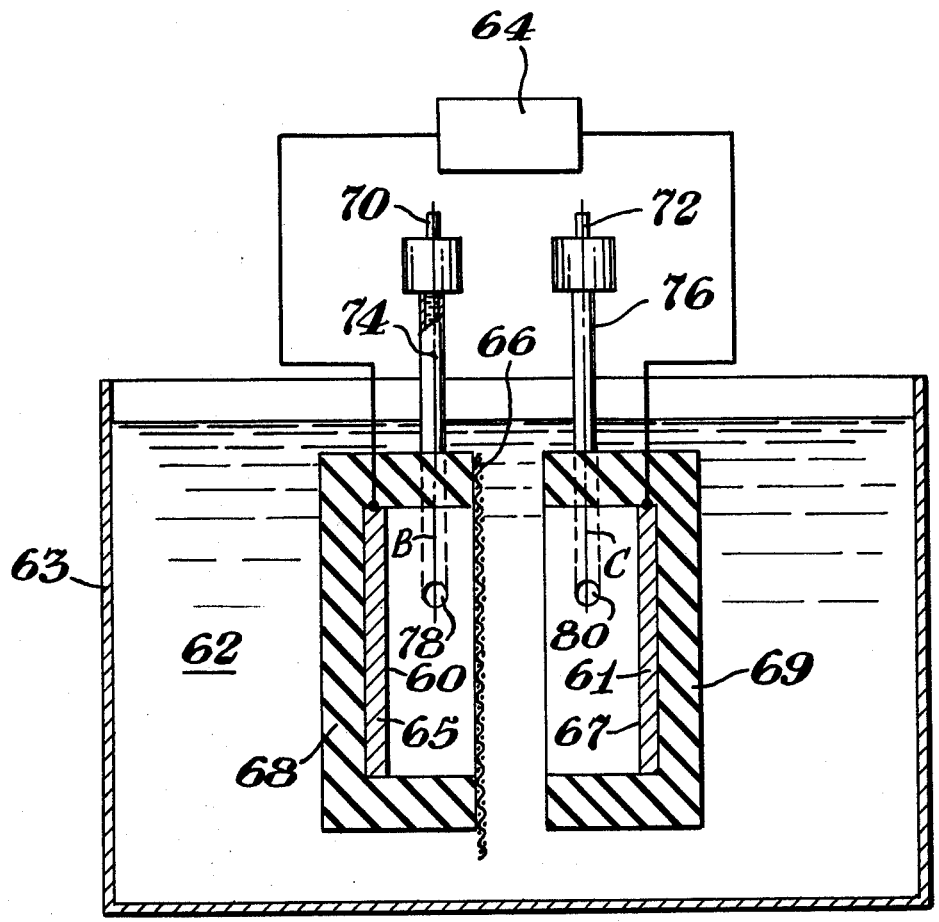

METHOD TO DETERMINE THE SUITABILITY OF DIAPHRAGM FOR USE IN AN ELECTROLYTIC CELL

CROSS-REFERENCE TO RELATED APPLICATION

This is a continuation-in-part of application Ser. No. 517,570, filed Oct. 24, 1974, now abandoned.

BACKGROUND OF THE INVENTION

This invention pertains to diaphragms and more in particular to a method to predetermine the suitability of a diaphragm for use in an electrolytic cell.

It has heretofore been difficult and occasionally impossible to predetermine whether a specific diaphragm would be suitable for employment in an electrolytic cell. It is known that the diaphragm construction material should be substantially nonreactive, i.e., physically and chemically inert with the electrolyte within the electrolytic cell; however, a means to accurately predetermine the effect of the configuration and surface characteristics of a specific foraminous diaphragm on the efficiency of a cell has been generally unknown. It is, therefore, highly desirable to provide a means to determine whether a diaphragm will be effective in a cell before insertion of such diaphragm into the electrolytic equipment.

SUMMARY OF THE INVENTION

A method to obtain a measurement indicative of the suitability of a diaphragm for use in an electrolytic cell has been developed. The method comprises impressing a known direct current electromotive force between a primary anode and a primary cathode immersed in a test cell containing an electrolyte. An electrical property across a predetermined portion of the electrolyte is measured with two measuring electrodes positioned between the primary anode and cathode and communicating with the predetermined portion of the electrolyte by a first salt bridge and a second salt bridge spaced apart a predetermined distance. The diaphragm to be measured is inserted between the measuring electrodes, and the electrical property across the predetermined portion of the electrolyte is remeasured. The change across the electrolyte resulting from insertion of the diaphragm can then be determined.

As used herein, the term diaphragm is defined as a porous barrier positioned between an anode and a cathode in an electrolytic cell. Such diaphragm can be, for example, constructed of asbestos, conductive porous plate or screen, sintered porous material, and like materials.

Since the efficiency of a diaphragm is at least partially dependent upon both the diaphragms's porosity and surface characteristics, such as roughness, a flow-through test alone (i.e., measuring the quantity of liquid which passes through a known area of diaphragm in a given time interval) to determine porosity is not generally an accurate measure of future diaphragm efficiency under operating electrolytic conditions. The present method of determining, for example, the electrical current passing through the pores in the diaphragm has been found to be dependent upon both the physical porosity and surface characteristics of the diaphragm. The voltage, resistance and/or electrical current measurements obtained in accord with the described method have surprisingly been found to provide an accurate indication of diaphragm effectiveness. The described method can be used for testing, for example, the suitability of the diaphragm for electrolytic purposes or as a means to periodically or continuously monitor the quality control in the production of and/or operation of such diaphragms.

BRIEF DESCRIPTION OF THE DRAWING

The single FIGURE shown in the drawing is a schematic representation of one embodiment of an apparatus useful in the practice of the present method.

DESCRIPTION OF THE PREFERRED EMBODIMENT

Referring to the drawing, primary electrodes, such as a primary anode 60 and a primary cathode 61 are immersed in an electrolyte 62 and connected to a power source 64. Suitable electrolytes are compatible with the primary electrodes 60 and 61 and with a diaphragm 66, and have a sufficient electrical conductivity to afford an accurate determination of the electrical effect of insertion of the diaphragm 66 into electrolyte 62. The primary electrodes 60 and 61 and electrolyte 62 are selected to form a cell capable of a reversible electrolytic reaction. Additionally, when a metallic diaphragm is tested, the conductivity of electrolyte 62 should preferably be such that insertion of diaphragm 66 into electrolyte 62 will produce an insufficient voltage change between the primary electrodes 60 and 61 to result in the metallic diaphragm 66 becoming a bipolar electrode. Examples of generally satisfactory electrolytes include inorganic, aqueous salt or acid electrolytic solutions, such as the chlorates, chlorides, nitrates and sulfates of metals. Suitable metals are, for example, alkali, alkaline earth and transition metals and preferably the alkali and alkaline earth metals, such as Li, Na, K, Rb, Cs, Be, Mg, Ca, Sr, and Ba. The materials employed as primary electrode material are those generally known in the art to be useful as electrodes, for example, graphite, Ru, Rh, Pd, Ag, Os, Ir, Pt and Au. Silver-silver chloride electrodes have proven to be especially suitable for use as primary electrodes and are preferred.

The primary electrodes 60 and 61 are suitably positioned within substantially electrically nonconductive retaining members 68 and 69 to space surface 65 of electrode 60 a predetermined distance, for example 1 inch apart, from surface 67 of electrode 61. The retaining members 68 and 69 can be constructed from, for example, a methyl acrylate plastic and adapted to direct substantially all of the electrical current passing between the electrodes 60 and 61 through the diaphragm 66 when such diaphragm is abuttingly detachably to the retaining members.

Two auxiliary calomel measuring electrodes 70 and 72 are connected to the electrolyte 62 by a first salt bridge 74 and a second salt bridge 76. Orifices 78 and 80 and salt bridges 74 and 76, respectively, pass through the retaining members 68 and 69 at a predetermined position between the primary electrodes 60 and 61 and communicate with the electrolyte 62. The orifices 78 and 80 are positioned apart to define a predetermined distance, for example ¾ inch, of electrolyte 62 between the center of such orifices as represented by center lines B and C.

The measuring or auxiliary electrodes 70 and 72 suitable for use in the present invention are well-known. For example, calomel, cadmium, hydrogen, mercury electrodes and the like can be used as measuring electrodes.

In the practice of the present invention, a direct current electromotive force is impressed between the primary anode 60 and the primary cathode 61 to produce a constant current flow between such primary electrodes.

The electromotive force impressed between the primary electrodes 60 and 61 should produce a voltage across the electrolyte which is less than the potential needed to decompose the electrolyte 62. For example, when an aqueous solution of NaCl is the electrolyte, the voltage across the electrolyte should be at least less than the decomposition potential of $H_2O$.

An electrical property, preferably the voltage, across the predetermined distance between the salt bridge orifices 78 and 80 is measured by the measuring electrodes 70 and 72. The resistance of the electrolyte 62 is determined by dividing the measured voltage between the measuring electrodes 70 and 72 by the known current flow.

The diaphragm 66 is placed in electrolyte 62 between the primary electrodes 60 and 61 and the salt bridge orifices 78 and 80 to thereby alter the electrical resistance between the measuring electrodes across the predetermined distance between salt bridge orifices 78 and 80. As aforementioned, the diaphragm 66 is placed in contact with the retaining member 68 in a manner suited to maximize the flow of current through the area of the diaphragm defined by the retaining member 68 and to minimize the passage of current through any openings at the interface between the surface of the retaining member 68 and the diaphragm 66 or around the edges of diaphragm 66.

The diaphragm 66 is positioned in electrolyte 62 between the primary electrodes 60 and 61 and the salt bridge orifices 78 and 80 to the measuring electrodes 70 and 72 to thereby alter the electrical resistance between the measuring electrodes. At a constant known current, the change in voltage across the predetermined portion of electrolyte 62, as measured by the measuring electrodes 70 and 72, is an amount characteristic of the porosity and surface characteristics or effectiveness of the diaphragm in an electrolytic diaphragm cell. Such diaphragm cells are suitable for electrolytically producing, for example, chlorine from a sodium chloride brine or, more preferably, a multivalent metal, such as titanium from titanium tetrachloride.

The present method can be employed to determine the uniformity of a diaphragm by using primary electrodes of such size and shape that the direct current produced therebetween passes only through a known area of the diaphragm. An electrical property, such as voltage, resistance or current flow, between the primary electrodes can be measured across a predetermined portion of the electrolyte before and after the insertion of the diaphragm between such primary electrodes. After each measurement, the diaphragm is moved with respect to the primary electrodes so that the subsequent measurement relates to a different portion of the diaphragm. Comparison of the results of two or more measurements will then reflect the uniformity or lack thereof in diaphragm permeability and surface characteristics. The tests can be carried out at any temperature or pressure, provided that they are held constant.

The hereinbefore method has been found to be acceptable for porous metallic screen, plate, or grid diaphragms and especially suitable for porous woven metal screen with a metal plating thereon.

The following examples illustrate the method of the present invention.

EXAMPLE 1

Employing an apparatus substantially as shown in the FIGURE, the suitability of a 2 inch diameter by 10 inch long cylindrical nickel plated, woven nickel screen for use as an electrolytic cell diaphragm was determined using a 0.1 molar sodium chloride aqueous electrolyte (reagent grade sodium chloride with a purity of 99.5 weight percent was dissolved in distilled water), two 1¼ by ½ by 1/16 inch thick rectangular silver-silver chloride primary electrodes spaced 1 inch apart, and two standard calomel electrodes suitably physically connected between the primary electrodes by salt bridges to afford measurement of a voltage impressed across a ¾ inch distance of sodium chloride solution. The silver-silver chloride electrodes were suitably mounted in methyl acrylate plastic frame adapted to permit insertion of the screen diaphragm between the electrodes.

A direct current electromotive force of sufficient voltage was impressed across the primary electrodes to produce a 2 milliampere (ma) current flow between the primary electrodes. The voltage and direct current across the measuring electrodes was determined before and after positioning the screen diaphragm between the electrodes. The tests were carried out at constant room temperature (about 20° C) and 1 atmosphere pressure. The voltage of the sodium chloride electrolyte was determined to be 68 millivolts (mv) and the current was verified at 2 milliamperes (ma) before insertion of the diaphragm. The voltage across the measuring electrodes increased to 93 millivolts after the diaphragm was inserted into the test cell; the current was maintained at a constant 2 milliamperes (ma).

The increase in voltage of 25 millivolts was calculated by standard methods to be equivalent to an increase in test cell resistance of 12.5 ohms or 0.276 inch of sodium chloride electrolyte between the electrodes.

Several diaphragms of identical material were tested as above described and employed in an electrolytic cell for producing titanium metal from titanium tetrachloride. The diaphragm coefficient ($C_d$) or diaphragm electrolyte equivalent (inches) was determined by the following formula and compared for the satisfactory and unsatisfactory diaphragms. A satisfactory diaphragm coefficient ($C_d$) range was thereby determined.

The diaphragm coefficient is represented by the formula:

$$C_d = \frac{\frac{V_{d+s}}{I_{d+s}} - \frac{V_s}{I_s}}{\frac{V_s}{I_s}} \times D \text{ where:}$$

$V_{d+s}$ is measured voltage (millivolts) across a predetermined portion of an electrolyte as determined by measuring electrodes communicating with the electrolyte by salt bridges with orifices to such salt bridges spaced apart by a predetermined distance (D), a diaphragm being positioned between said salt bridge orifices during operation $I_{d+s}$ is the measured electrical current (milliamperes) between the primary electrodes in the electrolyte with a diaphragm positioned as for $V_{d+s}$ $V_s$ is the measured voltage (millivolts) determined under identical conditions as for $V_{d+s}$ but without the diaphragm $I_s$ is the measured electrical current (milliamperes) between the primary electrodes in the electrolyte as determined for $I_{d+s}$ but without the diaphragm D is the predetermined distance between the salt bridge orifices

EXAMPLES 2-4

In a manner substantially in accordance with that described in Example 1, the coefficients ($C_d$) of other metal screen diaphragms were determined. The testing conditions and results are reported in Table I.

Additional metal screen diaphragms were evaluated by the present process using (a) 0.01 molar $H_2SO_4$ as the electrolyte and graphite as the primary electrodes and (b) 0.01 molar NaCl as the electrolyte and silver-silver chloride as the primary electrodes. Satisfactory results were obtained.

TABLE I

| | Diaphragm Coefficient Measurements | | | | |
|---|---|---|---|---|---|
| Example | $I_s$(ma) | $I_{d+s}$(ma) | $V_s$(mv) | $V_{d+s}$(mv) | $C_d$(inches) |
| 1 | 2 | 2 | 68 | 93 | 0.276 |
| 2 | 2 | 2 | 60 | 75 | 0.188 |
| 3 | 3 | 3 | 105.5 | 114 | 0.059 |
| 4 | 4 | 4 | 135 | 146 | 0.061 |

What is claimed is:

1. A method comprising
   (a) impressing a known direct current electromotive force between a primary anode and a primary cathode immersed in a test cell containing an electrolyte;
   (b) measuring an electrical property across a predetermined portion of said electrolyte with two measuring electrodes positioned between said primary anode and cathode and communicating with said predetermined portion of said electrolyte by a first salt bridge and a second salt bridge having orifices spaced apart a predetermined distance;
   (c) inserting a metallic diaphragm into said solution between said measuring electrodes said electrolyte having a conductivity such that the insertion of said metallic diaphragm produces a voltage change between said primary electrodes insufficient to convert said metallic diaphragm into a bipolar electrode; and
   (d) remeasuring the electrical property across said predetermined portion of said electrolyte as in (b).

2. The method of claim 1 wherein the electrolyte is an electrolytic solution containing a member selected from the group consisting of metal chlorates, metal chlorides, metal nitrates and metal sulfates.

3. The method of claim 2 wherein the metal is selected from the group consisting of alkali and alkaline earth metals.

4. The method of claim 2 wherein the electrolytic solution is aqueous sodium chloride.

5. The method of claim 4 wherein the electrolytic solution is 0.1 molar sodium chloride.

6. The method of claim 1 wherein the direct current electromotive force between primary electrodes is kept constant.

7. The method of claim 1 wherein the electrical property measured is voltage.

8. The method of claim 7 wherein the voltage across said predetermined portion of said electrolyte is less than that necessary to cause decomposition of the electrolyte.

9. The method of claim 1 wherein the electrical property measured is resistance.

10. The method of claim 1 wherein the electrical property measured is current flow.

11. The method of claim 1 including suitably positioning the diaphragm between the measuring electrodes to pass substantially all of the current passing between the primary anode and primary cathode through the diaphragm.

12. The method of claim 1 including suitably positioning the diaphragm apart from the primary anode and primary cathode and between the measuring electrodes to pass substantially all of the current passing between the primary anode and primary cathode through the diaphragm.

13. A method to predetermine the suitability of a metallic diaphragm for use in an electrolytic diaphragm cell comprising
   (a) impressing a known direct current electromotive force between a primary anode and a primary cathode immersed in a test cell containing an aqueous 0.1 molar sodium chloride solution;
   (b) measuring the voltage across a predetermined portion of said sodium chloride solution with two measuring electrodes positioned between said primary anode and cathode and communicating with said predetermined portion of said sodium chloride solution by a first salt bridge and a second salt bridge having orifices spaced apart a predetermined distance;
   (c) inserting the metallic diaphragm into said sodium chloride solution between said measuring electrodes;
   (d) remeasuring the voltage across said predetermined portion of said sodium chloride solution as in (b);
   (e) moving the diaphragm relative to the measuring electrodes to effect electrical current passage through another portion of the diaphragm;
   (f) remeasuring the voltage across said predetermined portion of said sodium chloride solution as in (b) to thereby obtain comparative voltage measurements indicative of diaphragm uniformity and suitability for use in an electrolytic cell.

14. The method of claim 13 wherein the primary anode is a silver electrode and the primary cathode is a silver chloride electrode.

15. The method of claim 13 wherein the measuring electrodes are calomel electrodes.

16. The method of claim 11 including abuttingly detachably attaching the diaphragm to substantially electrically nonconductive retaining means having the primary anode and primary cathode positioned therein.

* * * * *

UNITED STATES PATENT AND TRADEMARK OFFICE
CERTIFICATE OF CORRECTION

PATENT NO. : 4,090,924
DATED : May 23, 1978
INVENTOR(S) : Charles K. Bon

It is certified that error appears in the above—identified patent and that said Letters Patent are hereby corrected as shown below:

In column 1, line 55, delete "diaphragms's" and insert --diaphragm's--.

In Column 2, line 53, <u>after</u> the word "detachably" add --attached--.

In Column 5, example (c), line 44, insert a comma after the word electrodes.

Signed and Sealed this

Seventh Day of November 1978

[SEAL]

*Attest:*

RUTH C. MASON
*Attesting Officer*

DONALD W. BANNER
*Commissioner of Patents and Trademarks*